(12) United States Patent
Hsieh

(10) Patent No.: US 6,600,802 B1
(45) Date of Patent: Jul. 29, 2003

(54) IMAGE SPACE CORRECTION FOR MULTI-SLICE HELICAL RECONSTRUCTION WITH Z-SMOOTHING

(75) Inventor: Jiang Hsieh, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/113,159

(22) Filed: Apr. 1, 2002

(51) Int. Cl.[7] .................................................. A61B 6/03
(52) U.S. Cl. ................................ 378/4; 378/15; 378/62; 378/901
(58) Field of Search ........................... 378/4, 8, 15, 19, 378/62, 901

(56) References Cited

U.S. PATENT DOCUMENTS

| | | | |
|---|---|---|---|
| 6,061,420 A | * | 5/2000 | Strong et al. .................. 378/4 |
| 6,339,632 B1 | | 1/2002 | Besson |
| 6,418,184 B1 | | 7/2002 | Wang et al. |
| 6,421,411 B1 | | 7/2002 | Hsieh |

* cited by examiner

Primary Examiner—David V. Bruce
(74) Attorney, Agent, or Firm—Carl B. Horton, Esq.; Armstrong Teasdale LLP

(57) ABSTRACT

A method for facilitating a reduction of artifacts includes generating a first image of an object with a scanning system in native mode, generating a second image of the object with the scanning system with z-smoothing greater than any z-smoothing performed in native mode, and generating an artifact-candidate image by taking the difference between the first image and the second image.

36 Claims, 2 Drawing Sheets

IMAGE SPACE CORRECTION FOR MULTI-SLICE HELICAL RECONSTRUCTION WITH Z-SMOOTHING

BACKGROUND OF THE INVENTION

This invention relates to computed tomographic (CT) imaging, and more particularly to methods and apparatus for reducing imaging artifacts in an image generated using a multi-slice CT imaging system.

In order to achieve a reasonable level of artifact suppression, a nearly 30% degradation in slice thickness is encountered using at least one known method for artifact reduction. However, it is advantageous to maintain the same slice thickness for some clinical applications.

BRIEF DESCRIPTION OF THE INVENTION

In one aspect, a method for facilitating a reduction of artifacts is provided. The method includes generating a first image of an object with a scanning system in native mode, generating a second image of the object with the scanning system with z-smoothing greater than any z-smoothing performed in native mode, and generating an artifact-candidate image by taking the difference between the first image and the second image.

In another aspect, a method for facilitating a reduction of artifacts includes generating a first image $I_o$ of an object with a scanning system in native mode, generating a second image $I_s$ of the object with the scanning system with z-smoothing greater than any z-smoothing performed in native mode, and generating an artifact-candidate image $I_a$ by taking the difference between the first image and the second image. The method also includes removing high-frequency content from the generated artifact-candidate image to generate an artifact image $I_n$ by removing all objects smaller than a pre-defined threshold size, and generating a mask image m(x,y) using at least one of a $m_o(x,y)$ and a $m_s(x,y)$ according to:

$$m_o(x, y) = \begin{cases} 0, & I_o(x, y) \le t_{low} \\ \frac{I_o(x, y) - t_{low}}{t_{high} - t_{low}}, & t_{low} < I_o(x, y) \le t_{high} \\ 1, & I_o(x, y) > t_{high} \end{cases}$$

$$m_s(x, y) = \begin{cases} 0, & I_s(x, y) \le t_{low} \\ \frac{I_s(x, y) - t_{low}}{t_{high} - t_{low}}, & t_{low} < I_s(x, y) \le t_{high} \\ 1, & I_s(x, y) > t_{high} \end{cases}$$

where the mask $m(x,y)=m_o(x,y)m_s(x,y)$, where $m_o(x,y)$ represents a mask for the first image, $m_s(x,y)$ represents a mask for the second image, $t_{low}$ and $t_{high}$ are predetermined thresholds. The method also includes generating a corrected image $I_c$ according to:

$I_c(x,y)=I_o(x,y)-s \times m(x,y) \times I_n(x,y)$, where s is a scaling factor.

In yet another aspect, a computer is programmed to generate a first image of an object with a scanning system in native mode, generate a second image of the object with the scanning system with z-smoothing greater than any z-smoothing performed in native mode, and generate an artifact-candidate image by taking the difference between the first image and the second image.

In a further aspect, a computer is programmed to generate a first image $I_o$ of an object with a scanning system in native mode, generate a second image $I_s$ of the object with the scanning system with z-smoothing greater than any z-smoothing performed in native mode, and generate an artifact-candidate image $I_a$ by taking the difference between the first image and the second image. The computer is also programmed to remove high-frequency content from the generated artifact-candidate image to generate an artifact image $I_n$ by removing all objects smaller than a pre-defined threshold size and generate a mask image m(x,y) using at least one of a $m_o(x,y)$ and a $m_s(x,y)$ according to:

$$m_o(x, y) = \begin{cases} 0, & I_o(x, y) \le t_{low} \\ \frac{I_o(x, y) - t_{low}}{t_{high} - t_{low}}, & t_{low} < I_o(x, y) \le t_{high} \\ 1, & I_o(x, y) > t_{high} \end{cases}$$

$$m_s(x, y) = \begin{cases} 0, & I_s(x, y) \le t_{low} \\ \frac{I_s(x, y) - t_{low}}{t_{high} - t_{low}}, & t_{low} < I_s(x, y) \le t_{high} \\ 1, & I_s(x, y) > t_{high} \end{cases}$$

where the mask $m(x,y)=m_o(x,y)m_s(x,y)$, where $m_o(x,y)$ represents a mask for the first image, $m_s(x,y)$ represents a mask for the second image, $t_{low}$ and $t_{high}$ are predetermined thresholds. The computer is further programmed to generate a corrected image $I_c$ according to:

$I_c(x,y)=I_o(x,y)-s \times m(x,y) \times I_n(x,y)$, where s is a scaling factor.

In another aspect, a computed tomographic (CT) imaging system for reconstructing an image of an object is provided. The imaging system includes a detector array, at least one radiation source, and a computer coupled to the detector array and the radiation source. The computer is configured to generate a first image of an object with a scanning system in native mode, generate a second image of the object with the scanning system with z-smoothing greater than any z-smoothing performed in native mode, and generate an artifact-candidate image by taking the difference between the first image and the second image.

In a still further aspect, a computed tomographic (CT) imaging system for reconstructing an image of an object is provided. The imaging system includes a detector array, at least one radiation source, and a computer coupled to the detector array and the radiation source. The computer is configured to generate a first image $I_o$ of an object with a scanning system in native mode, generate a second image $I_s$ of the object with the scanning system with z-smoothing greater than any z-smoothing performed in native mode, and generate an artifact-candidate image $I_a$ by taking the difference between the first image and the second image. The computer is also configured to remove high-frequency content from the generated artifact-candidate image to generate an artifact image $I_n$ by removing all objects smaller than a pre-defined threshold size, and to generate a mask image m(x,y) using at least one of a $m_o(x,y)$ and a $m_s(x,y)$ according to:

$$m_o(x, y) = \begin{cases} 0, & I_o(x, y) \le t_{low} \\ \frac{I_o(x, y) - t_{low}}{t_{high} - t_{low}}, & t_{low} < I_o(x, y) \le t_{high} \\ 1, & I_o(x, y) > t_{high} \end{cases}$$

-continued $$m_s(x, y) = \begin{cases} 0, & I_s(x, y) \leq t_{low} \\ \dfrac{I_s(x, y) - t_{low}}{t_{high} - t_{low}}, & t_{low} < I_s(x, y) \leq t_{high} \\ 1, & I_s(x, y) > t_{high} \end{cases}$$

where the mask $m(x,y) = m_o(x,y) m_s(x,y)$, where $m_o(x,y)$ represents a mask for the first image, $m_s(x,y)$ represents a mask for the second image, $t_{low}$ and $t_{high}$ are predetermined thresholds. The computer is also configured to generate a corrected image $I_c$ according to:

$I_c(x,y) = I_o(x,y) - s \times m(x,y) \times I_n(x,y)$, where s is a scaling factor.

DETAILED DESCRIPTION OF THE INVENTION

Figure 1:
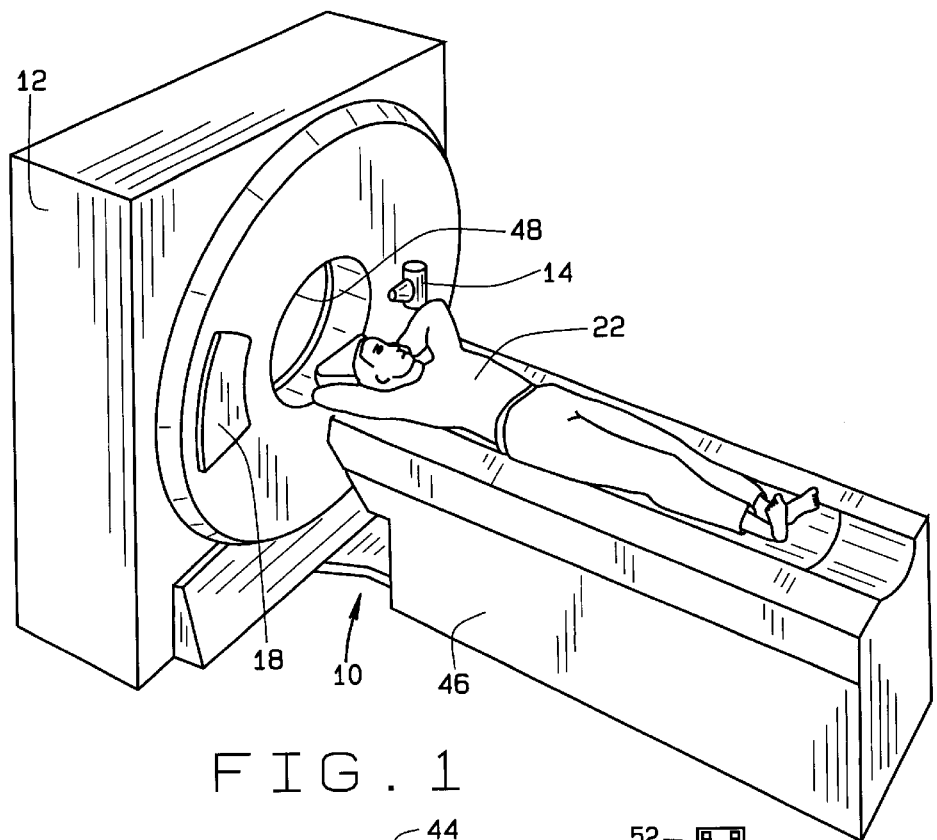
FIG. 1 is a pictorial view of a CT imaging system.

In some CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated beam radiation received at the detector array is dependent upon the attenuation of an x-ray beam by the object. Each detector element of the array produces a separate electrical signal that is a measurement of the beam attenuation at the detector location. The attenuation measurements from all the detectors are acquired separately to produce a transmission profile.

In third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered back projection process, the data is weighted according to a helical weighing factor, which is a function of both the gantry angle and detector angle. The helical weighting algorithms also scale the data according to a scaling factor, which is a function of the distance between the x-ray source and the object. The weighted and scaled data is then processed to generate CT numbers and to construct an image that corresponds to a two dimensional slice taken through the object. For some known helical algorithms, the helical weighting functions are determined based on the geometric information of the scanner. In other words, the weighting function does not change from scan-to-scan or patient-to-patient, so long as the scanning protocol remains the same. Although these algorithms have been performing somewhat satisfactorily in a clinical setting, recent investigations have revealed severe image artifacts. Studies have shown that all of the existing algorithms perform roughly the same in terms of image artifacts.

Alternatively, a new set of projection data can be interpolated from the original helical data. A filtered backprojection is then applied to the interpolated projection. The backprojection operation can be applied in either 2D or 3D (cone beam).

For helical algorithms developed up to date, images are reconstructed by weighting the projections prior to filtered backprojection. Once an image is generated, no more processing is performed (with the exception of "ringfix" to remove rings and "IBO" to remove bone beam-hardening artifacts). Consequently, the ability of an algorithm to combat multi-slice helical image artifacts relies solely on the derived weighting functions, method of interpolation, accuracy of backprojection, and other factors in the helical reconstruction process. This limitation is known in both single-slice helical as well as multi-slice helical algorithms.

These artifacts can be suppressed by applying low-pass filtering along the z-axis. Low-pass filtering can be carried out either in the projection space or in the image space. This approach, however, merely trades off image artifacts with the slice thickness. And, in order to achieve reasonable artifact suppression, a nearly 30% degradation in slice thickness is encountered. For all helical scan applications, it is advantageous to maintain the same slice thickness for some clinical applications.

Figure 2:
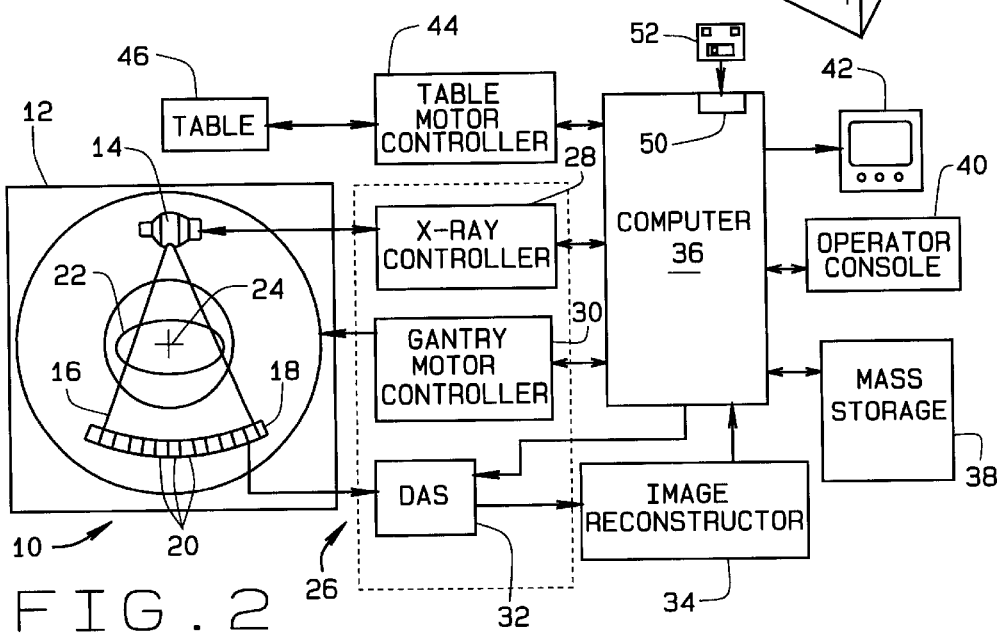
FIG. 2 is a block schematic diagram of the system illustrated in FIG. 1.

Referring to FIGS. 1 and 2, a multi-slice scanning imaging system, for example, computed tomography (CT) imaging system 10, is shown as including a gantry 12 representative of a "third generation" CT imaging system. Gantry 12 has an x-ray source 14 that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22. Each detector element 20 produces an electrical signal that represents the intensity of an impinging x-ray beam and hence the attenuation of the beam as it passes through object or patient 22. During a scan to acquire x-ray projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 so that projection data corresponding to a plurality of quasi-parallel or parallel slices can be acquired simultaneously during a scan.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive or CD-ROM drive, for reading instructions and/or data from a computer-readable medium 52, such as a floppy disk or CD-ROM. In another embodiment, computer 36 executes instructions stored in firmware (not shown). Computer 36 is programmed to perform functions described herein, but other programmable circuits can be likewise programmed. For example, in one embodiment, DAS 32 performs functions described herein. Accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits. Additionally, although described in a medical setting, it is contemplated that the benefits of the invention accrue to all CT systems including industrial CT systems such as, for example, but not limited to, a baggage scanning CT system typically used in a transportation center such as, for example, but not limited to, an airport or a rail station.

Figure 3:
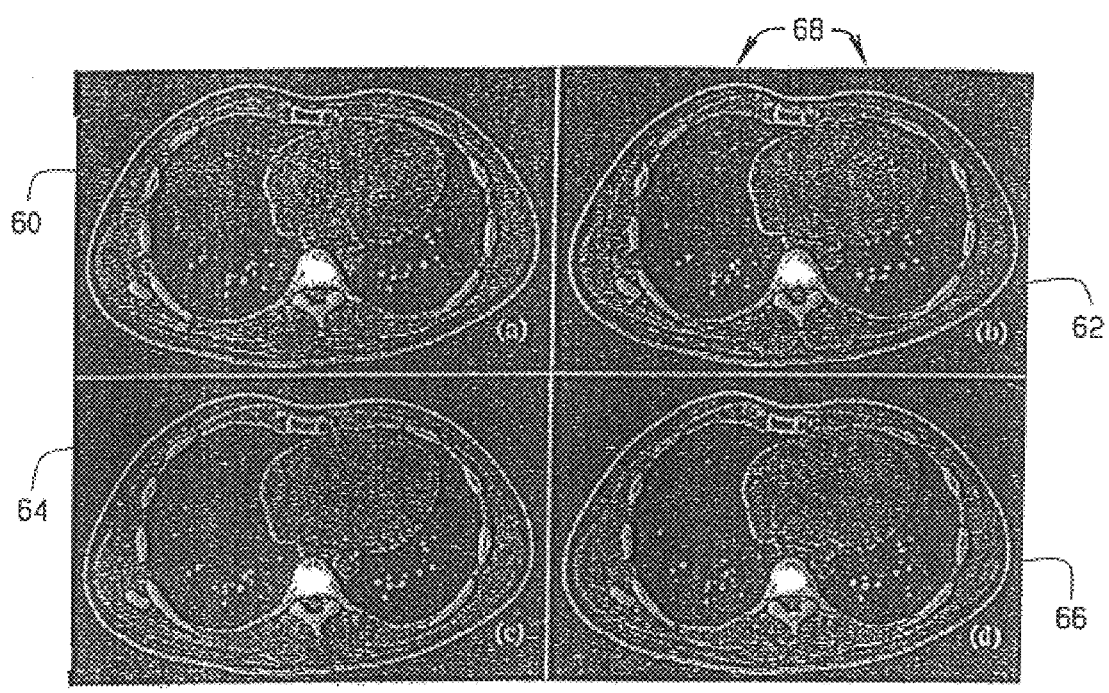
FIG. 3 illustrates generated images of a patient scan.

For each final image to be produced with CT system 10, two initial images are first generated, an image in native mode (e.g., using a Generalized Helical Interpolation (GHI) algorithm without any z-smoothing or with some level of smoothing to achieve a desired slice thickness, "first image") and an image with a slight amount of additional smoothing beyond what has been done for the first image, (e.g., using a GHI algorithm with some additional z-smoothing, "second image"). Therefore, as used herein, "native mode" means using a GHI algorithm without any z-smoothing and using a GHI algorithm with some level of z-smoothing to achieve a desired slice thickness. The parameter of the second image is selected such that it has minimal broadening of the slice-sensitivity profile with some level of artifact suppression. For example, in an exemplary embodiment, a 13% slice broadening for the second image is selected. As an example, FIG. 3 illustrates generated images of a patient scan collected in 8×2.5 mm mode at a pitch of 7:1 (window width, ww=600). More specifically, FIG. 3 includes a reconstructed with a GHI algorithm image 60, a reconstructed with slight z-smoothing image 62, a reconstructed with uniform image space correction image 64, and a reconstructed with selective image space correction image 66. Image 62 still contains substantial amount of image artifacts near a plurality of ribs 68.

Next, an artifact-candidate image $I_a(x,y)$ is generated by subtracting the two images. Since the second image is generated with minimum slice broadening, the difference image (i.e., the artifact-candidate image) contains mainly the image artifacts due to helical interpolation. Mathematically, it can be described by the following equation: $I_a(x,y)=I_o(x,y)-I_s(x,y)$, where $I_o(x,y)$ represents the first image, and $I_s(x,y)$ represents the second image.

To facilitate a preservation of spatial resolution in the z direction, the artifact-candidate image is further processed to remove high-frequency contents in the image, producing an artifact-only image $I_n(x,y)$, also referred herein as the artifact image. The removal of high frequency content can be carried out with many existing algorithms. For example, the image space can be searched to remove any object that is smaller than a pre-defined threshold. This is mainly based on the observation that helical artifacts are, in general, low-frequency in nature and they tend to spread out over a larger region. This operation can be denoted mathematically by an operator according to $I_n(x,y)=I_a(x,y)-f[I_a(x,y)]$, where the f operator identifies all the features in the image that satisfy a pre-determined set of conditions (for example, size, intensity, and shape constraints). To further preserve spatial resolution in the image, a-priori information is used to assist the processing. For example, helical interpolation induced artifacts are typically unlikely to appear inside the lobes of the lung. Therefore, an intensity of the reconstructed pixel is used to provide a mask to the correction process. For example, the following mask generating function is used to produce a mask image, $m(x,y)$:

$$m_o(x,y) = \begin{cases} 0, & I_o(x,y) \leq t_{low} \\ \dfrac{I_o(x,y) - t_{low}}{t_{high} - t_{low}}, & t_{low} < I_o(x,y) \leq t_{high} \\ 1, & I_o(x,y) > t_{high} \end{cases}$$

$$m_s(x,y) = \begin{cases} 0, & I_s(x,y) \leq t_{low} \\ \dfrac{I_s(x,y) - t_{low}}{t_{high} - t_{low}}, & t_{low} < I_s(x,y) \leq t_{high} \\ 1, & I_s(x,y) > t_{high} \end{cases}$$

$$m(x,y)=m_o(x,y)m_s(x,y)$$

where $m_o(x,y)$ represents a mask for the first image, $m_s(x,y)$ represents a mask for the second image, $t_{low}=-500$ Houndsfield Units (HU) and $t_{high}=-200$ HU are predetermined thresholds. The corrected image, $I_c(x,y)$, is then $I_c(x,y)=I_o(x,y)-s \times m(x,y) \times I_n(x,y)$, where s is a scaling factor. In one embodiment, $m(x,y)$ is not determined using both $m_o(x,y)$ and $m_s(x,y)$. Rather $m(x,y)$ is determined using either $m_o(x,y)$ or $m_s(x,y)$.

Other methods can also be used to preserve spatial resolution in the correction process. For example, one can use feature identification to remove any features in $I_n(x,y)$ that are unlikely to be helical induced artifacts, since helical artifacts are typically low-frequency shadings.

In an exemplary embodiment, s is about 1.8. In other embodiments, s is between about 1.5 and about 2.1 or between about 1.2 and about 2.4. Alternatively, s is less than about 1.2 or greater than about 2.4. The parameter s can also be dynamically adjusted based on the helical scan parameters (such as helical pitch and detector aperture) and patient anatomy. Images 64 and 66 show the corrected images without and with the masking process (image 64 is with m(x,y)=1)). At a soft-tissue display window, both schemes performed nearly identically in terms of artifact suppression, and artifacts near the ribs are significantly reduced.

Figure 4:
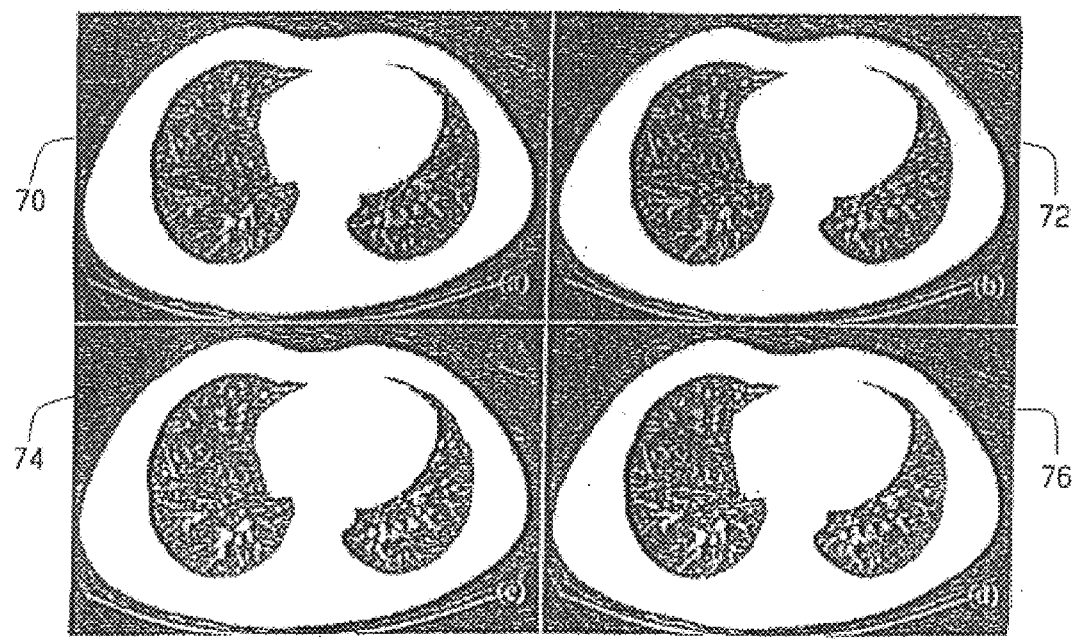
FIG. 4 illustrates a plurality of images of a patient scan corrected with masking.

FIG. 4 illustrates a plurality of images of a patient scan collected in 8×2.5 mm mode at a pitch of 7:1 (ww=600) corrected with masking as described above. More specifically, FIG. 4 includes a reconstructed with a GHI algorithm and masked image 70, a reconstructed with slight z-smoothing and masked image 72, a reconstructed with uniform image space correction and masked image 74, and a reconstructed with selective image space correction and masked image 76. FIG. 4 illustrates that the herein described correction with masking preserves the original features in the lung region, indicating a preservation of spatial resolution.

Although particular embodiments of the invention have been described and illustrated in detail, it is to be clearly understood that the same is intended by way of illustration and example only and is not to be taken by way of limitation. In addition, the CT system described herein is a "third generation" system in which both the x-ray source and detector rotate with the gantry. However, many other CT systems including "fourth generation" systems wherein the detector is a full-ring stationary detector and only the x-ray source rotates with the gantry may be used. While the invention has been described in terms of various specific embodiments, those skilled in the art will recognize that the invention can be practiced with modification within the spirit and scope of the claims.

What is claimed is:

1. A method for facilitating a reduction of artifacts, said method comprising:
generating a first image of an object with a scanning system in native mode;
generating a second image of the object with the scanning system with z-smoothing greater than any z-smoothing performed in native mode; and
generating an artifact-candidate image by taking the difference between the first image and the second image.

2. A method in accordance with claim 1 said generating a second image comprises generating a second image of the object with the scanning system with z-smoothing and a broader slice-sensitivity profile than the first image.

3. A method in accordance with claim 1 said generating a second image comprises generating a second image of the object with the scanning system with z-smoothing and a broader slice-sensitivity profile than the first image by no more than twenty percent.

4. A method in accordance with claim 1 said generating a second image comprises generating a second image of the object with the scanning system with z-smoothing and a broader slice-sensitivity profile than the first image by no more than twenty percent and no less than ten percent.

5. A method in accordance with claim 1 said generating a second image comprises generating a second image of the object with the scanning system with z-smoothing and a broader slice-sensitivity profile than the first image by approximately thirteen percent.

6. A method in accordance with claim 1 further comprising removing high-frequency content and other object related features from the generated artifact-candidate image to generate an artifact image.

7. A method in accordance with claim 6 wherein said removing high-frequency content comprises removing all objects smaller than a pre-defined threshold size.

8. A method in accordance with claim 1 further comprising utilizing a mask image based on a pre-determined set of conditions to correct the artifact-candidate image.

9. A method in accordance with claim 6 further comprising utilizing a mask image based on a pre-determined set of conditions to correct the artifact image.

10. A method in accordance with claim 9 further comprising generating a mask image m(x,y) using at least one of a $m_o(x,y)$ and a $m_s(x,y)$ according to:

$$m_o(x, y) = \begin{cases} 0, & I_o(x, y) \le t_{low} \\ \dfrac{I_o(x, y) - t_{low}}{t_{high} - t_{low}}, & t_{low} < I_o(x, y) \le t_{high} \\ 1, & I_o(x, y) > t_{high} \end{cases}$$

$$m_s(x, y) = \begin{cases} 0, & I_s(x, y) \le t_{low} \\ \dfrac{I_s(x, y) - t_{low}}{t_{high} - t_{low}}, & t_{low} < I_s(x, y) \le t_{high} \\ 1, & I_s(x, y) > t_{high} \end{cases}$$

where the mask $m(x,y)=m_o(x,y)m_s(x,y)$, where $m_o(x,y)$ represents a mask for the first image, $m_s(x,y)$ represents a mask for the second image, $t_{low}$ and $t_{high}$ are pre-determined thresholds, $I_o$ represents the first image, and $I_s$ represents the second image.

11. A method in accordance with claim 10 wherein to correct the artifact image, said method further comprises generating a corrected image according to:

$I_c(x,y)=I_o(x,y)-s \times m(x,y) \times I_n(x,y)$, where s is a scaling factor, $I_c$ represents the corrected image, and $I_n$ represents the artifact image.

12. A method for facilitating a reduction of artifacts, said method comprising:
generating a first image $I_o$ of an object with a scanning system in native mode;
generating a second image $I_s$ of the object with the scanning system with z-smoothing greater than any z-smoothing performed in native mode;
generating an artifact-candidate image $I_a$ by taking the difference between the first image and the second image;
removing high-frequency content and object related features from the generated artifact-candidate image to generate an artifact image $I_n$ by removing all objects that are at least one of smaller than a pre-defined threshold size and match a pre-defined feature;
generating a mask image m(x,y) using at least one of a $m_o(x,y)$ and a $m_s(x,y)$ according to:

$$m_o(x, y) = \begin{cases} 0, & I_o(x, y) \le t_{low} \\ \dfrac{I_o(x, y) - t_{low}}{t_{high} - t_{low}}, & t_{low} < I_o(x, y) \le t_{high} \\ 1, & I_o(x, y) > t_{high} \end{cases}$$

$$m_s(x, y) = \begin{cases} 0, & I_s(x, y) \le t_{low} \\ \dfrac{I_s(x, y) - t_{low}}{t_{high} - t_{low}}, & t_{low} < I_s(x, y) \le t_{high} \\ 1, & I_s(x, y) > t_{high} \end{cases}$$

where the mask $m(x,y)=m_o(x,y)m_s(x,y)$, where $m_o(x,y)$ represents a mask for the first image, $m_s(x,y)$ represents a mask for the second image, $t_{low}$ and $t_{high}$ are pre-determined thresholds; and generating a corrected image $I_c$ according to:

$I_c(x,y)=I_o(x,y)-s \times m(x,y) \times I_n(x,y)$, where s is a scaling factor.

13. A computer programmed to:
generate a first image of an object with a scanning system in native mode;
generate a second image of the object with the scanning system with z-smoothing greater than any z-smoothing performed in native mode; and
generate an artifact-candidate image by taking the difference between the first image and the second image.

14. A computer in accordance with claim 13 further programmed to generate a second image of the object with the scanning system with z-smoothing and a broader slice-sensitivity profile than the first image.

15. A computer in accordance with claim 13 further programmed to generate a second image of the object with the scanning system with z-smoothing and a broader slice-sensitivity profile than the first image by no more than twenty percent.

16. A computer in accordance with claim 13 further programmed to generate a second image of the object with the scanning system with z-smoothing and a broader slice-sensitivity profile than the first image by no more than twenty percent and no less than ten percent.

17. A computer in accordance with claim 13 further programmed to generate a second image of the object with the scanning system with z-smoothing and a broader slice-sensitivity profile than the first image by approximately thirteen percent.

18. A computer in accordance with claim 13 further programmed to remove high-frequency content and other object related features from the generated artifact-candidate image to generate an artifact image.

19. A computer in accordance with claim 18 further programmed to remove all objects that are at least one of smaller than a pre-defined threshold size and match a pre-defined feature.

20. A computer in accordance with claim 13 further programmed to utilize a mask image based on a pre-determined set of conditions to correct the artifact-candidate image.

21. A computer in accordance with claim 13 further programmed to utilize a mask image based on a pre-determined set of conditions to correct the artifact image.

22. A computer in accordance with claim 21 further programmed to generate a mask image m(x,y) using at least one of a $m_o(x,y)$ and a $m_s(x,y)$ according to:

$$m_o(x, y) = \begin{cases} 0, & I_o(x, y) \leq t_{low} \\ \dfrac{I_o(x, y) - t_{low}}{t_{high} - t_{low}}, & t_{low} < I_o(x, y) \leq t_{high} \\ 1, & I_o(x, y) > t_{high} \end{cases}$$

$$m_s(x, y) = \begin{cases} 0, & I_s(x, y) \leq t_{low} \\ \dfrac{I_s(x, y) - t_{low}}{t_{high} - t_{low}}, & t_{low} < I_s(x, y) \leq t_{high} \\ 1, & I_s(x, y) > t_{high} \end{cases}$$

where the mask $m(x,y)=m_o(x,y)m_s(x,y)$, where $m_o(x,y)$ represents a mask for the first image, $m_s(x,y)$ represents a mask for the second image, $t_{low}$ and $t_{high}$ are pre-determined thresholds, $I_o$ represents the first scan, and $I_s$ represents the second image.

23. A computer in accordance with claim 22 further programmed to generate a corrected image according to:

$I_c(x,y)=I_o(x,y)-s \times m(x,y) \times I_n(x,y)$, where s is a scaling factor, $I_c$ represents the corrected image, and $I_n$ represents the artifact image.

24. A computer programmed to:
generate a first image $I_o$ of an object with a scanning system in native mode;
generate a second image $I_s$ of the object with the scanning system with z-smoothing greater than any z-smoothing performed in native mode;
generate an artifact-candidate image $I_a$ by taking the difference between the first image and the second image;
remove high-frequency content from the generated artifact-candidate image to generate an artifact image $I_n$ by removing all objects that are at least one of smaller than a pre-defined threshold size and match a pre-defined feature;
generate a mask image m(x,y) using at least one of a $m_o(x,y)$ and a $m_s(x,y)$ according to:

$$m_o(x, y) = \begin{cases} 0, & I_o(x, y) \leq t_{low} \\ \dfrac{I_o(x, y) - t_{low}}{t_{high} - t_{low}}, & t_{low} < I_o(x, y) \leq t_{high} \\ 1, & I_o(x, y) > t_{high} \end{cases}$$

$$m_s(x, y) = \begin{cases} 0, & I_s(x, y) \leq t_{low} \\ \dfrac{I_s(x, y) - t_{low}}{t_{high} - t_{low}}, & t_{low} < I_s(x, y) \leq t_{high} \\ 1, & I_s(x, y) > t_{high} \end{cases}$$

where the mask $m(x,y)=m_o(x,y)m_s(x,y)$, where $m_o(x,y)$ represents a mask for the first image, $m_s(x,y)$ represents a mask for the second image, $t_{low}$ and $t_{high}$ are predetermined thresholds; and
generate a corrected image $I_c$ according to:

$I_c(x,y)=I_o(x,y)-s \times m(x,y) \times I_n(x,y)$, where s is a scaling factor.

25. A computed tomographic (CT) imaging system for reconstructing an image of an object, said imaging system comprising:
a detector array;
at least one radiation source; and
a computer coupled to said detector array and said radiation source, said computer configured to:
generate a first image of an object with a scanning system in native mode;
generate a second image of the object with the scanning system with z-smoothing greater than any z-smoothing performed in native mode; and
generate an artifact-candidate image by taking the difference between the first image and the second image.

26. A CT imaging system in accordance with claim 25 wherein said computer is further programmed to generate a second image of the object with the scanning system with z-smoothing greater than any z-smoothing performed in native mode and a broader slice-sensitivity profile than the first image.

27. A CT imaging system in accordance with claim 25 wherein said computer is further programmed to generate a second image of the object with the scanning system with z-smoothing greater than any z-smoothing performed in native mode and a broader slice-sensitivity profile than the first image by no more than twenty percent.

28. A CT imaging system in accordance with claim 25 wherein said computer is further programmed to generate a second image of the object with the scanning system with z-smoothing greater than any z-smoothing performed in native mode and a broader slice-sensitivity profile than the first image by no more than twenty percent and no less than ten percent.

29. A CT imaging system in accordance with claim 25 wherein said computer is further programmed to generate a second image of the object with the scanning system with z-smoothing greater than any z-smoothing performed in native mode and a broader slice-sensitivity profile than the first image by approximately thirteen percent.

30. A CT imaging system in accordance with claim 25 wherein said computer is further programmed to remove high-frequency content and other object related features from the generated artifact-candidate image to generate an artifact image.

31. A CT imaging system in accordance with claim 30 wherein said computer is further programmed to remove all objects that are at least one of smaller than a pre-defined threshold size and match a pre-defined feature.

32. A CT imaging system in accordance with claim 25 wherein said computer is further programmed to utilize a mask image based on a pre-determined set of conditions to correct the artifact-candidate image.

33. A CT imaging system in accordance with claim 25 wherein said computer is further programmed to utilize a mask image based on a pre-determined set of conditions to correct the artifact image.

34. A CT imaging system in accordance with claim 33 wherein said computer is further programmed to generate a mask image $m(x,y)$ using at least one of a $m_o(x,y)$ and a $m_s(x,y)$ according to:

$$m_o(x, y) = \begin{cases} 0, & I_o(x, y) \le t_{low} \\ \dfrac{I_o(x, y) - t_{low}}{t_{high} - t_{low}}, & t_{low} < I_o(x, y) \le t_{high} \\ 1, & I_o(x, y) > t_{high} \end{cases}$$

$$m_s(x, y) = \begin{cases} 0, & I_s(x, y) \le t_{low} \\ \dfrac{I_s(x, y) - t_{low}}{t_{high} - t_{low}}, & t_{low} < I_s(x, y) \le t_{high} \\ 1, & I_s(x, y) > t_{high} \end{cases}$$

where the mask $m(x,y)=m_o(x,y)m_s(x,y)$, where $m_o(x,y)$ represents a mask for the first image, $m_s(x,y)$ represents a mask for the second image, $t_{low}$ and $t_{high}$ are pre-determined thresholds, $I_o$ represents the first scan, and $I_s$ represents the second image.

35. A CT imaging system in accordance with claim 34 wherein said computer is further programmed to generate a corrected image according to:

$I_c(x,y)=I_o(x,y)-s \times m(x,y) \times I_n(x,y)$, where s is a scaling factor, $I_c$ represents the corrected image, and $I_n$ represents the artifact image.

36. A computed tomographic (CT) imaging system for reconstructing an image of an object, said imaging system comprising:

a detector array;

at least one radiation source; and a computer coupled to said detector array and said radiation source, said computer configured to:

generate a first image $I_o$ of an object with a scanning system in native mode;

generate a second image $I_s$ of the object with the scanning system with z-smoothing greater than any z-smoothing performed in native mode;

generate an artifact-candidate image $I_a$ by taking the difference between the first image and the second image;

remove high-frequency content and other object related features from the generated artifact-candidate image to generate an artifact image $I_n$ by removing all objects that are at least one of smaller than a pre-defined threshold size and match a pre-defined feature;

generate a mask image $m(x,y)$ using at least one of a $m_o(x,y)$ and a $m_s(x,y)$ according to:

$$m_o(x, y) = \begin{cases} 0, & I_o(x, y) \le t_{low} \\ \dfrac{I_o(x, y) - t_{low}}{t_{high} - t_{low}}, & t_{low} < I_o(x, y) \le t_{high} \\ 1, & I_o(x, y) > t_{high} \end{cases}$$

$$m_s(x, y) = \begin{cases} 0, & I_s(x, y) \le t_{low} \\ \dfrac{I_s(x, y) - t_{low}}{t_{high} - t_{low}}, & t_{low} < I_s(x, y) \le t_{high} \\ 1, & I_s(x, y) > t_{high} \end{cases}$$

where the mask $m(x,y)=m_o(x,y)m_s(x,y)$, where $m_o(x,y)$ represents a mask for the first image, $m_s(x,y)$ represents a mask for the second image, $t_{low}$ and $t_{high}$ are pre-determined thresholds; and generate a corrected image $I_c$ according to:

$I_c(x,y)=I_o(x,y)-s \times m(x,y) \times I_n(x,y)$, where s is a scaling factor.

* * * * *